United States Patent
Epstein

(10) Patent No.: US 7,323,471 B1
(45) Date of Patent: Jan. 29, 2008

(54) TOPICAL AZATHIOPRINE FOR THE TREATMENT OF ORAL AUTOIMMUNE DISEASES

(75) Inventor: Joel B. Epstein, Blaine, WA (US)

(73) Assignee: DOR Biopharma, Inc., Ewing, NJ (US)

(*) Notice: Subject to any disclaimer, the term of this patent is extended or adjusted under 35 U.S.C. 154(b) by 0 days.

(21) Appl. No.: 09/433,418

(22) Filed: Nov. 4, 1999

Related U.S. Application Data

(60) Provisional application No. 60/148,804, filed on Aug. 13, 1999.

(51) Int. Cl.
*A61K 31/519* (2006.01)

(52) U.S. Cl. .................................................. 514/262.1

(58) Field of Classification Search ................ 514/262, 514/262.1
See application file for complete search history.

(56) References Cited

U.S. PATENT DOCUMENTS

| | | | |
|---|---|---|---|
| 3,056,785 A | 2/1962 | Hitchings et al. | 260/252 |
| 4,996,193 A | 2/1991 | Hewitt et al. | 514/11 |
| 5,204,329 A | 4/1993 | Ackerman et al. | 514/15 |
| 5,310,545 A | 5/1994 | Eisen | 424/49 |
| 5,540,931 A * | 7/1996 | Hewitt et al. | |
| 5,578,609 A * | 11/1996 | Batt et al. | 514/314 |
| 5,637,616 A * | 6/1997 | Sharpe et al. | |
| 5,639,759 A | 6/1997 | Magolda et al. | 514/285 |
| 5,691,343 A | 11/1997 | Sandborn | 514/262 |
| 5,716,648 A | 2/1998 | Halskov et al. | 424/682 |
| 5,733,915 A | 3/1998 | Sandborn et al. | 514/262 |
| 5,905,081 A | 5/1999 | Sandborn | 514/262 |

FOREIGN PATENT DOCUMENTS

| WO | WO-97/31921 | * 9/1997 |
|---|---|---|

OTHER PUBLICATIONS

Eggleston, et al., Treatment of Aphthous Ulceration with Topical Azathioprine, British Journal of Oral Surgery (1972), 9: 233-236.*

Halliday, GM, Knight, BA, Muller, HK. Reduction In Murine Langerhans Cell ATPase Staining Following Topical But Not Systemic Treatment with Steroid and Non-Steroid Immunosuppressants. Br J Dermatol 1986; 114:83-89.

Mornington, B. The Place of Azathioprine in the Treatment of Auto-Immune Diseases. Leb Med J 1973; 26(1): 21-30.

Woo, SB, Lee, SJ, Schubert, MM. Graft-vs.-host disease. Crit Rev Oral Biol Med 1997; 8(2):201-216.

(Continued)

*Primary Examiner*—San-ming Hui
(74) *Attorney, Agent, or Firm*—Catalyst Law Group; David M. Kohn

(57) ABSTRACT

A method for treating or preventing symptoms associated with oral autoimmune diseases comprises treating a patient with an oral topical formulation of azathioprine or a pharmaceutically acceptable salt thereof. The azathioprine formulation may be used in the form of an oral rinse to topically treat areas of oral tissue inflammation and ulceration caused by the onset of oral autoimmune diseases, such as GVHD. The oral topical formulation of azathioprine may also be used in combination with other topical or systemic immunosuppressants or anti-inflammatory drugs.

8 Claims, 6 Drawing Sheets

OTHER PUBLICATIONS

Schubert, MM, Sullivan, KM. Recognition, incidence, and management of oral graft-versus-host disease. NCI Monogr 1990; (9):135-143.

Nakamura, S, Hiroki, A, Shinohara, M, et al. Oral involvement in chronic graft-versus-host disease after allogeneic bone marrow transplantation. Oral Surg Oral Med Oral Pathol Oral Radiol Endod 1996; 82(5):556-563.

Epstein JB, Reece, DE. Topical cyclosporin A for treatment of oral chronic graft-versus-host disease. Bone Marrow Transplant 1994; 13:81-86.

Epstein JB, Truelove, EL. Topical cyclosporin in a bioadhesive for treatment of oral lichenond mucosal reaction Oral Surg Oral Med Oral Pathol Oral Radiol Endod 1996; 82:532-536.

Sandborn WJ. A review of immune modifier therapy for inflammatory bowel disease: azathioprine, 6-mercaptourine, cyclosporin, and methotrexate. Am J Gastroenterol 1996; 91(3):423-433.

Winklestein A. The effects of azathioprine and 6-MP on immunity. J Immunopharmacol 1979; 1:429-454.

Brogan M, Hiserodt J, Oliver M, et al. The effect of 6-mercaptopurine on natural killer-cell activities in Crohn's disease. J Clin Immunol 1985; 5:204-11.

Brogan M, Stevens R, Hiserodt J, et al. Effects of 6-MP on the impaired in vivo humoral responsiveness in Crohn's disease. Gastroenterol 1984; 86:A1035.

Lozada F. Prednisone and azathioprine in the treatment of patients with vesiculoerosive oral diseases. Oral Surg Oral Med Oral Pathol 1981; 52(3):257-260.

Robinson JR, Lozada-Nur F, Frieden I. Oral pemphigus vulgaris. A review of the literature and a report on the management of the 12 cases. Oral Surg Oral Med Oral Pathol Oral Radiol Endod 1997; 84:349-355.

Lear, JT, English, JSC. Erosive and generalized lichen planus responsive to azathioprine. Clin Exper Derm 1996; 21:56-57.

Allen LV Jr, Erickson MA. Stability of acetazolamide, allopurinol, azathioprine, clonazepam, and flucytosine in extemporaneously compounded oral liquids. Am J Health-Syst Pharm 1996; 53:1944-1949.

Eggleston DJ, Nally FF. Treatment of aphthous ulceration with topical azathioprine. A double blind trial. Br J Oral Surg 1972; 9(3):233-236.

Suchko VI, Mashchenko IS. Local use of an azathioprine suspension in a dimexide solution in the combined treatment of parodontosis. Stomologica (Mosk) 1981; 60(3): 28-30.

Elliot JH, Leibowitz HM. Chemotherapeutic immunosuppression of the corneal graft reaction. 3 Topical azathioprine. Arch Opthalmol 1966; 76(5):709-711.

Mackay IR, Bignell JL, Smith PH, Crawford BA. Prevention of corneal-graft failure with the immunosuppressive drug azathioprine. Lancet 1967; 514 (2):479-482.

Choi PM, Targan SR. Immunomodulator therapy in inflammatory bowel disease. Dig Dis Sci 1994; 39(9):1885-1892.

Stotland BR, Lichtenstein GR. Newer treatments for inflammatory bowel disease. Prim Care 1996; 3(3):577-608.

Zins BJ, Sandborn WJ, McKinney JA, et al. A dose-ranging study of azathioprine pharmacokinetics after single-dose administration of a delayed-release oral formulation. J Clin Pharmacol 1997; 37:38-46.

Vans Os EC, Zins WJ, Sandborn WJ, et al. Azathioprine pharmacokinetics after intravenous, oral, delayed release oral and rectal foam administration. Gut 1996; 39:63-68.

Epstein JB, Priddy RW, Sherlock CH. Hairy leukoplakia-like lesions in immunosuppressed patients following bone marrow transplantation. Transplantation 1988; 46:462-4.

Epstein JB, Sherlock CH, Wolber RA. Hairy leukoplakia after bone marrow transplantation. Oral Surg Oral Med Oral Pathol 1993; 75:690-5.

Scully, C, Paes de Llmeida, O, Porter, SR, Gilkes, JJH. Pemphigus vulgaris: the manifestations and long-term management of 55 patients with oral lesions. Br J Dermatol 1999; 140:84-89.

Lever, WF. Pemphigus and pemphigoid. A review of the advances made since 1964. J Amer Acad Dermatol. 1979; 1(1):2-31.

Anstey, A, Lear, JT. Azathioprine: clinical pharmacology and current indications in autoimmune disorders. BioDrugs 1998; 9(1):33-47.

Glied, M, Rico, JM. Treatment of autoimmune blistering diseases. Dermatol Clin 1999; 17(2):431-330.

Eisen, D, Ellis, CN, et al. Effect of Topical Cyclosporine Rinse on Oral Lichen Planus. New Engl J Med 1990; 323(5):290-294.

Ho, VC and Conklin, RJ. Effect of Topical Cyclosporine Rinse on Oral Lichen Planus. New Engl J Med 1991; 325(6):435.

Eisen, D, Griffiths, CEM et al. Cyclosporin Wash for Oral Lichen Planus. Lancet 1990; 335:535-536.

Eisen, D, Ellis, CN, Voorhees, JJ. Topical cyclosporine for oral bullous disorders. J Amer Acad Dermatol 1990; 23(5):936-937.

Eisen, D, Ellis, CN. Topical Cyclosporine for Oral Mucosal Disorders. J Amer Acad Dermatol 1990; 23(6):1259-1264.

Volc-Platzer, B, Hönigsmann, H et al. Photochemotherapy Improves Chronic Cutaneous Graft-Versus-Host Disease.

Farthing, PM, Maragou, P et al. Characteristics Of The Oral Lesions In Patients With Cutaneous Recurrent Erythema Multiforme. J Oral Path Med 1995; 24:9-13.

Plauth, M, Jenss, H, Meyle, J. Oral Manifestations of Crohn's Disease: An Analysis of 79 Cases. J Clin Gastroenterol 1991; 13(1):29-71.

Chemical Abstracts Services, No. 66CA:64312, Rhomburg et al., "Immunosuppressive Therapy in Internal Medicine", Schweiz. Med. Wochenschr. vol. 97(8), pp. 255-259, 1967.

Chemical Abstracts Services, No. 72CA:39197, Salmon et al., "Treatment of autoimmune diseases with antimitotic agents", Arch. Belg. Dermatol. Syphiligr., vol. 24(3) pp. 297-309, 1968.

* cited by examiner

TOPICAL AZATHIOPRINE FOR THE TREATMENT OF ORAL AUTOIMMUNE DISEASES

This application claims priority to U.S. Provisional Application No. 60/148,804, filed on Aug. 13, 1999.

FIELD OF THE-INVENTION

The present invention relates to a method for treating persistent symptomatic oral autoimmune diseases through the use of topical azathioprine ("AZA") or a derivative thereof. More particularly, the present invention relates to a method wherein an AZA solution or suspension is used to topically treat areas of oral tissue inflammation and ulceration caused by the onset of an oral autoimmune disease. The method of the present invention may also be performed prophylactically, to inhibit development of symptoms associated with the onset of an oral autoimmune disease. The method is described with particular reference to oral chronic graft-versus-host disease ("GVHD").

BACKGROUND OF THE INVENTION

Autoimmune diseases occur when the body's immune defenses overcome the normal tolerance mechanisms and attack the body's cells, organs and systems. Autoimmune diseases may be caused by an exogenous factor, or may arise spontaneously. Autoimmune diseases include a broad range of conditions that may be organ-specific or general. Among the organ-specific autoimmune disorders are rheumatoid arthritis and pemphigoid. Among the general autoimmune disorders are system lupus erythematosus and graft-versus-host disease ("GVHD").

A number of autoimmune disorders produce oral symptoms. These include oral lupus, oral lichen planus [12], pemphigus vulgaris [24], oral aphthous stomatitis [14], pemphigoid [25], and GVHD [1,2,3]. In addition, there are immune consequences associated with acquired immune deficiency syndrome (AIDS), such as mucosal lichenoid changes and aphthae. These diseases are characterized by aberrant infiltration and activation by cells of the immune system, and exhibit various oral symptoms, including mucous membrane lesions, blisters, and erosions.

Oral lichen planus is a relatively common disease that can result in severe or chronic lesions involving mucosal surfaces, including the mouth [28]. These lesions can be very painful and persistent, lasting on the order of years. Oral lichen planus is often self-limiting; however, where treatment is required, systemic or intra-lesional steroid treatments are helpful. Topical steroids are only partially effective, and can lead to significant side-effects.

Pemphigus vulgaris is a mucocutaneous disease that often involves oral lesions. The distinctive symptom is blistering between certain layers of the epidermis. The blisters may be very painful and, if left untreated, may result in sepsis, cachexia, and major fluid and electrolyte imbalances reminiscent of those seen in severe burn patients [28]. Current treatment involves high doses of systemic corticosteroids and/or immunosuppressants, and because of the side-effects associated with these drugs hospitalization is often necessary.

Pemphigoid is divided into two forms—bullous pemphigoid and cicatricial pemphigoid. Of the two, cicatricial pemphigoid far more often involves oral lesions than bullous pemphigoid. Oral lesions are common in cicatricial pemphigoid, occurring in approximately 90% of cases [25]. Chronic mucosal lesions often lead to scarring, and ocular lesions may lead to blindness [28]. Treatment requires high levels of systemic corticosteroids and immunosuppressants, but even when given over long periods of time such treatments may be only partially effective.

Oral aphthous ulceration ("canker sores") is a condition characterized by inflammatory lesions that occur principally in the mouth, although it can affect any mucosal surface. Although the cause is unknown, it has been postulated that an autoimmune antigen-antibody reaction occurs [14]. Present treatment includes oral anaesthetics, improved hygiene and occasionally oral suspensions of tetracyclines and systemic and/or topical steroids [28].

Bone marrow transplantation ("BMT") is a common treatment for many hematologic malignancies and immune deficiency states. BMT is used with increasing frequency for salvage therapy of many solid malignancies. Between 12,000 and 15,000 bone marrow transplants are performed each year in the United States. Of these, the number of allogeneic (donor) transplantations is estimated to be between 5,500 and 7,500. GVHD is a major complication of allogeneic BMT, occurring in 25% to 70% of BMT patients, despite GVHD prophylaxis [1].

GVHD occurs when genetically disparate but immunologically active lymphoid cells (T-cells) are transplanted into an immunosuppressed recipient incapable of rejecting the graft. The transplanted T-lymphocytes recognize histocompatibility antigens of host tissues as foreign, become sensitized, proliferate, and directly or through secondary mechanisms attack recipient tissue. The primary target organs of GVHD are the skin, gastrointestinal tract, and liver. GVHD can occur as a result of organ transplantation or bone marrow transplantation.

Two forms of GVHD, acute and chronic, have been described and differ in their onset and their clinical features. Acute GVHD (aGVHD) occurs in the first 100 days post-BMT, with the median day of onset being 19 days post-transplant. The target organs of aGVHD include the skin, gastrointestinal tract, and the liver. In contrast, chronic (cGVHD) presents a far more varied multiorgan "autoimmunity" clinical picture that includes liver dysfunction, pulmonary fibrosis, sclerodermatous skin changes, oral and gastrointestinal mucosa changes, and a reduced production of tears and saliva. The onset of cGVHD occurs between 100 and 400 days post-BMT. Because it involves many organs, cGVHD can cause significant morbidity and disability.

GVHD is an example of a general autoimmune disorder with oral involvement. Oral findings are seen in both acute and chronic GVHD. Oral involvement ranges between 33% and 75% for patients with aGVHD and up to about 80% for those with cGVHD. In some patients, oral symptoms are the most significant clinical finding of GVHD. Oral lesions in GVHD may be lichenoid or lupus-like in appearance. Oral findings of aGVHD include painful desquamative, erythematous, and ulcerative mucosal lesions [1,2]. In cGVHD, they are lichenoid with associated erythema and ulcerations; additionally, they may be associated with sicca syndrome characterized by xerostomia and progressive salivary gland atrophy [1,2,3]. Oral complications include pain due to the mucosal changes, altered or reduced taste, and may have a potential impact on speech, deglutition, and use of oral prostheses (when present). Oral infection, particularly due to candida species, and dental demineralization and caries may also occur.

The conventional management of oral cGVHD consists of systemic immunosuppressive therapies combined with proper oral hygiene and the judicious use of topical steroids

[1,2]. However, for patients with oral cGVHD as the most significant clinical finding, the use of systemic immunosuppressants may result in immunosuppression of the host with attendant systemic complications. In addition, some patients experience considerable and refractory oral complications, even with maximum doses of systemic immunosuppressants.

Topical formulations of some immunosuppressants, such as cyclosporin A ("CsA"), have been used in the management of various autoimmune conditions [4,5]. U.S. Pat. No. 4,996,193 to Hewitt et al. discloses formulations for the topical application of CsA to skin tissue in the treatment of autoimmune diseases, T-cell mediated immune diseases, and inflammatory conditions. In addition, methods of use of these formulations, with or without accompanying systemic doses of CsA, are discussed. Topical formulations of CsA have also been employed in the management of oral cGVHD [4]. However, some GVHD patients do not respond well to systemic or topical formulations of CsA [4]. Furthermore, topical formulations of CsA are ineffective unless administered at relatively high concentrations. As a result, the high cost of CsA makes the use of these methods prohibitively expensive.

The generically available drug azathioprine ("AZA") (brand name: Imuran) is one of the most widely used cytotoxic immunosuppressants in clinical medicine. AZA is a purine analog that is quickly metabolized in vivo to 6-mercaptopurine (6-MP), and thereafter to 6-thioguanine nucleotide (6-TNG). These compounds act as purine antagonists that interfere with the synthesis of DNA, RNA and protein [6]. They are known to act as immunomodulators, due to their selective effects on T cells and T cell-dependent responses [7] and their effects on natural killer cell activity [8] and humoral responsiveness [9]. AZA is commonly prescribed for many autoimmune diseases, including severe rheumatoid arthritis, systemic lupus erythmatosus, myasthenia gravis, autoimmune chronic active hepatitis, and pemphigus vulgaris [10,26]. In addition, AZA is commonly prescribed to inhibit the immune responses that cause rejection of organ transplants. The role of systemic AZA in the management and prevention of inflammatory bowel disease (IBD) has been well characterized [18,19], and AZA has been shown to be efficacious in the long term management of inflammatory bowel diseases, such as Crohn's disease, with less long term toxicity than that associated with corticosteroids [19]. Systemic AZA has proven effective as a steroid-sparing immunosuppressant in the management of chronic oral vesiculoerosive diseases, such as pemphigus vulgaris and lichen planus [10, 11, 12]. AZA has been shown to be stable as a compounded liquid (50 mg/ml solution retained at least 96% of the initial concentration for 60 days at 25° C.) [14], and further is much less expensive than other commonly used immunosuppressants, such as cyclosporin A.

Systemic AZA is usually administered either orally or intravenously. Oral administration is the preferred route in most cases, since the intravenous preparation is an extreme irritant. The dosage depends on the clinical requirements and the hematological tolerance of the patient, but is usually in the range of 1-4 mg/kg/day.

However, when administered systemically, AZA also induces a wide variety of significant side-effects. The side effects of systemic therapy with azathioprine [6] can be categorized as either allergic or non-allergic in nature. The allergic-type reactions appear to be dose-independent and may include the following symptoms: rash, fever, pancreatitis, arthralgias, malaise, nausea, and diarrhea. The non-allergic effects are thought to be dose-dependent and include leukopenia, thrombocytopenia, hepatitis, and infection. AZA is also thought to be a mutagen and a carcinogen [26]. In light of these significant adverse effects, dosing and toxicity monitoring (including a complete blood count and liver enzyme studies) are required to monitor the patient's therapy. Weekly complete blood counts are recommended for the first 8 weeks of systemic AZA treatment, and patients are monitored closely for any evidence of infection, unexpected bruising or bleeding, or other manifestations of bone marrow depression [26,27].

Recent pharmacokinetic studies of alternate formulations of azathioprine for treatment of inflammatory bowel disease (IBD) have been undertaken to provide methods of local drug delivery in the lower intestine with reduced bioavailability and resultant systemic toxicity. In one study, AZA was administered as a delayed-release oral capsule and showed improved ileocolonic delivery with dramatically reduced systemic bioavailability [20]. In another study, four different formulations of AZA were compared, including intravenous, oral, delayed-release oral, and rectal foam administration [21]. U.S. Pat. Nos. 5,691,343 and 5,905,081 to Sandborn disclose methods for treating IBD by topical administration of AZA, using, for example, either rectal administration by an enema or oral administration of delayed release unit dosage form.

There exist only sporadic reports of the use of topical AZA in oral diseases, such as aphthous stomatitis and parodontosis [14,15], and as immunosuppressive therapy in the prevention of corneal graft rejection [16,17]. To date, the effectiveness of topical routes of AZA administration is unclear. While topical AZA was reported to have some beneficial effect in the treatment of parodontosis [15], topical AZA was ineffective in the treatment of corneal graft rejections [16] and aphthous stomatitis [14]. Therefore, a need remains for an effective means to combat oral GVHD and other oral autoimmune diseases that does not implicate the serious side-effects encountered with conventional systemic AZA administration routes.

SUMMARY OF THE INVENTION

The present invention describes a method for treating oral GVHD or other oral autoimmune diseases. The method comprises administering to a patient in need of such treatment an effective amount of a topical solution or suspension of azathioprine. Preferably, AZA is present in the solution or suspension at concentration of between about 0.5-50 mg/ml, and is administered at a dosage of between 50-250 mg/day. More preferably, the dosage administered is between 100-200 mg/day. The patient may either rinse the oral cavity for a period of time with AZA and thereafter swallow to maintain a systemic dose or, alternatively, expectorate after rinsing with little or no swallowing of the solution or suspension. AZA may be concurrently administered with a topical or systemic anti-inflammatory compound or another immunosuppressant. Furthermore, AZA may be administered prior to the onset of an autoimmune disease, to inhibit development of the symptoms associated with such a disease. For example, AZA may be administered prior to or after a bone marrow transplant, before symptoms of either aGVHD or cGVHD develop. AZA is much less expensive than other commonly used immunosuppressants, and further may be effective in patients who do not respond to these other immunosuppressants. Furthermore, topical AZA will not promote oral cadidiasis, a common problem with topical steroids.

It is therefore an object of the present invention to provide a method for treating or preventing an autoimmune disease of the mouth, comprising applying to the mouth of a patient in need of such treatment an effective amount of azathioprine or a pharmaceutically acceptable salt thereof. The azathioprine is administered as often as required, and in a sufficient concentration, to provide alleviation or reduction in symptoms. The azathioprine is contacted with the surfaces of the mouth for a period of at least one minute, which allows direct contact of the drug with the afflicted areas at a higher local concentration than would be possible with systemic administration of the same drug.

BRIEF DESCRIPTION OF THE DRAWINGS

FIG. 1A: left side view of the cheek mucosal surface. FIG. 1B: right side view of the cheek mucosal surface. FIG. 1C: right lateral border of the tongue and tongue tip. FIG. 1D: left lateral border of the tongue and tongue tip.

FIG. 2A: left side view of the cheek mucosal surface. FIG. 2B: right side view of the cheek mucosal surface. FIG. 2C: right lateral border of the tongue and tongue tip. FIG. 2D: left lateral border of the tongue and tongue tip.

FIG. 3A: left side view of the cheek mucosal surface. FIG. 3B: right side view of the cheek mucosal surface. FIG. 3C: right lateral border of the tongue and tongue tip. FIG. 3D: left lateral border of the tongue and tongue tip.

DETAILED DESCRIPTION OF THE PREFERRED EMBODIMENTS

Figure 1A:
FIGS. 1A-1D show persisting oral GVHD in a patient prior to initiation of AZA as a topical rinse.

The present invention describes a method for treating oral GVHD or other oral autoimmune diseases. The method comprises administering to a patient in need of such treatment an effective amount of a topical solution or suspension of azathioprine (AZA)

An "effective amount" is an amount that when administered is effective to prevent or ameliorate the symptoms or progression of the oral autoimmune disease. The AZA may be administered alone or with a pharmaceutically acceptable carrier. The AZA may be administered in the form of an effective derivative or precursor of azathioprine, or in the form of a pharmaceutically acceptable salt of azathioprine. An effective derivative or precursor of AZA is one that, like AZA, is converted to 6-MP and thereafter to 6-TNG, or, alternatively, is a compound that is closely related structurally to AZA such that it undergoes similar biochemical reactions in the body as AZA to produce similar effects when used to treat oral autoimmune diseases or conditions. The method of the present invention may also be used to prevent or inhibit the development of symptoms associated with an autoimmune disease, by administering to a patient an effective amount of a solution or suspension of AZA prior to the onset of such symptoms.

The term "topical solution or suspension" means a solution or suspension that can be administered to the external surface of the affected oral area. The solution or suspension may contain coloring or flavoring as needed to increase patient acceptance. It is also envisioned that the azathioprine may be administered in the form of a lozenge, lollipop, pellet, cream, gel, ointment, quick dissolving tablet, gum, mucosal adhesive, or any other solid form that will permit contact of the azathioprine with the oral mucosal surfaces. By "pharmaceutically acceptable", what is meant is that the carrier or salt is compatible with the other components of the AZA-containing solution or suspension and is not deleterious or harmful to the patient.

Those of skill in the art will appreciate that the dosage administered will vary due to a number of factors, such as, for example, the particular disease being treated; whether the treatment is therapeutic or prophylactic in nature; the pharmacodynamic characteristics of the particular agent; the duration of the topical application; the age, health, and weight of the patient; the nature and extent of the symptoms; the kind of concurrent treatment; and the effect desired. As a general rule, the amount of topical oral AZA administered will range from about 0.5 to about 50 mg/ml in the solution or suspension being used. Furthermore, a daily dosage in the range of 50-250 mg/day may be administered. Also as a general rule, the solution or suspension will be held in the mouth for at least one minute, with vigorous agitation to rinse as much of the surfaces of the oral cavity as possible. After rinsing, the solution or suspension may be expectorated, or may be swallowed to enhance the systemic concentration of azathioprine. Deviations from these ranges that produce the therapeutic effects envisioned by the practitioner without significant harm to the patient are considered to be within the scope of the present claims. The method is simple and maximizes contact with the afflicted areas of the patient. Furthermore, AZA is much less expensive than other commonly used immunosuppressant drugs, such as cyclosporin A.

The oral topical formulation of AZA may be used either alone or in combination with a pharmaceutically acceptable systemic dose of AZA. By "in combination with", it is meant that the components are administered at the same time or sequentially in any order at different points in time. When administered at different points in time, the components should be administered sufficiently closely in time to produce the desired therapeutic effect. The systemic dose of AZA may be administered in any appropriate manner, including swallowing AZA in a solid form, such as a pill, tablet, caplet, or the like. Alternatively, the systemic AZA may be administered in the form of an oral rinse of a solution or suspension containing azathioprine. The systemic dose of azathioprine may also be administered, intravenously, via a suppository, or in any other appropriate manner. In still another embodiment, the oral topical formulation of AZA may be used in combination with a pharmaceutically acceptable topical or systemic dose of an anti-inflammatory agent and/or an immunosuppressant other than AZA. Examples of a steroidal anti-inflammatory agent that may be used in the method of the present invention include, without limitation, hydrocortisone, betamethasone dipropionate, betamethasone valerate, fluocinolone acetonide, triamcinolone acetonide, prednisone, methylprednisolone, or prednisolone. Examples of a nonsteroidal anti-inflammatory agent include, without limitation, indomethacin, sulindac, ibuprofen, aspirin, naproxen and tolmetin. Examples of an immunosuppressant other than AZA that may be used in the method of the present invention include, without limitation, the cyclosporins, such as cyclosporin A, cyclophosphamide, the macrolide FK-506, deoxyspergualin, thalidomide, methotrexate, bredinin, deoxyspergualin, and didemnin B. The doses of these antiinflammatory agents and/or immunosuppressants are those known to the practitioner in each case to be effective without an undesirable level of adverse effects on the patient. Antiinflammatory agents and immunosuppressants other than those listed here may be used in the method of the present invention, so long as they are pharmaceutically acceptable.

Other oral autoimmune diseases or oral diseases with autoimmune characteristics may also be treated by the method of the present invention. Examples of such oral diseases include, without limitation, oral lichen planus, pemphigoid, pemphigus vulgaris, oral lupus, aphthous stomatitis, and lichenoid changes and aphthae associated with acquired immune deficiency syndrome (AIDS). As noted above, the oral topical formulation of AZA may be used either alone or in combination with a systemic dose of AZA. In still another embodiment, the oral topical formulation of AZA may be used in combination with a topical or systemic dose of an anti-inflammatory agent and/or an immunosuppressant. The anti-inflammatory agent and/or immunosuppressant may be as listed above. Those of skill in the art will recognize that the dosages of the anti-inflammatory agent and/or immunosuppressant administered for each of the diseases may vary, as described above, and that the desired dosages are those that produce the desired therapeutic effects without significant harm to the patient.

The oral rinse disclosed in the method of the present invention avoids the serious side-effects associated with systemic administration of AZA. The oral rinse method of the present invention also allows better contact of AZA with the afflicted portions of the oral cavity than might be possible using gels, creams or ointments. Furthermore, the oral rinse procedure is likely to be more acceptable to patients than the use of such gels, creams, or ointments. However, such formulations may be particularly useful for the treatment of localized oral lesions. Therefore, it is intended that such formulations may also be used advantageously in the method of the present invention.

The following data further illustrate the present invention in greater detail but are not intended to be construed as limiting the scope of the invention in any way.

Case Report:

We report a severe case of chronic oral GVHD refractory to systemic and topical therapies, which was managed successfully with the addition of a topically applied liquid formulation of the immunosuppressive drug azathioprine (AZA).

A 34-year-old male presented with pancytopenia in late October, 1994, and was diagnosed with aplastic anemia. He received a matched sibling donor bone marrow transplant on Nov. 1, 1994, and was seen monthly following transplant. He had continuing difficulties with GVHD, including oral involvement.

The patient's oral status was evaluated at day 100 post-BMT in March, 1995. Oral findings were consistent with pseudomembranous candidiasis, and an ulceration on the left cheek was consistent with minor trauma. There were no clinical findings suggestive of oral GVHD, and saliva volumes were not decreased. Acute (grade II) GVHD (skin and liver) was treated with systemic corticosteroids. Therapy with systemic cyclosporin (3 mg/kg/b.i.d.) and prednisone (1 mg/kg/day) was commenced May, 1995.

Persisting oral problems developed, including recurrent infections (herpes simplex virus (HSV) and candida) and ulcerations secondary to GVHD, and had a major negative impact on the post-BMT course. Leukoplakia involving the lateral borders of the tongue, consistent with hairy-like leukoplakia, developed. In May, 1995, he reported several days of sore mouth involving the cheeks and gums. Oral changes included findings consistent with GVHD and reactivation of HSV. HSV and candida were confirmed on culture. The clinical findings consistent with HSV improved with the prescription of acyclovir. However, findings of oral GVHD persisted despite continuing systemic immunosuppressive therapy, with lichenoid changes associated with moderate erythema on the non-keratinized mucosa of the cheeks, tongue, and lips. Multiple dilated salivary ducts were visualized on the soft palate. Ulcerations of 3-4 mm in diameter were present on the lateral borders, the dorsum, and the tip of the tongue. Due to findings of increasing GVHD and possible candidosis, a biopsy of the lip mucosa and minor salivary glands was completed, which demonstrated changes consistent with GVHD. Biopsy of the ulcer on the cheek was consistent with HSV.

GVHD was difficult to control despite many modifications in both systemic and topical immunosuppression. Topical corticosteroids including dexamethasone rinse (0.4 mg/ml), fluocinonide gel, and dermovate cream were ineffective. Topical cyclosporin preparations were ineffective (rinse) or poorly tolerated (gel). Benefit was noted with administration of high-dose systemic steroids, although this was associated with undesirable side effects (hypertension, myopathy, weight gain, and candidosis). Intravenous immunoglobulin was added in April of 1996 because of systemic hypogammaglobulinemia. Following development of an esophageal stricture (November, 1996), Tacrolimus (FK506) was begun along with AZA tablets (100 mg/day), and cyclosporin was discontinued. The prednisone dose was maintained relatively constant after November 1996 (10 mg/day). On Oct. 24, 1997, increasing oral sensitivity associated with oral GVHD was reported. Extensive lichenoid striae with moderate erythema and ulceration involving the lateral tongue on the right and left and the right cheek was seen. A second oral biopsy of lip mucosa and minor salivary glands was completed, which was interpreted as grade II GVHD. Hydroxychloroquine was added (400 mg/day) in November 1997, but was discontinued in December 1997, due to diarrhea.

Figure 1B:
Figure 1C:
Figure 1D:

In December 1997, AZA was given as a suspension (25 mg q.i.d., rinsed 1-2 minutes then swallowed to maintain the systemic dose of 100 mg/day). The AZA suspension was made by combining AZA powder with a cherry flavored methylcellulose (1%) suspending vehicle to a final concentration of 5 mg/ml. The oral findings present prior to the prescription of the AZA suspension are shown in FIGS. 1A-1D. The oral symptoms included erythema, lichenoid striations and ulceration, moderate erythema involving the right buccal mucosa, ulceration and erythema involving the left cheek, and extensive irregular ulceration involving the left lateral border of the tongue with associated intense erythema. Minor ulcerations and erythema involving the right lateral border of the tongue were also evident.

Figure 2A:
FIGS. 2A-2D show improving findings of oral GVHD associated with use of topical AZA rinse in the same patient as in FIGS. 1A-1D.
Figure 2B:
Figure 2C:
Figure 2D:

There was clinical evidence of improvement in both oral ulceration and erythema and oral sensitivity with the use of the AZA suspension (FIGS. 2A-2D). Lichenoid changes were decreased, and a single ulceration measuring 5×22 mm remained on the left lateral border of the tongue, with reduction in erythema in all oral sites of involvement and resolution of oral ulcers and reduction in size of the residual ulceration on the left lateral tongue. The ulcer had thickened, rolled borders, although its central area appeared to be partially re-epithelialized.

In early March, 1998, the patient stopped the AZA rinse, returning to the same dose by tablet, and within 10 days increased mouth discomfort was reported. Examination revealed an ulceration on the left lateral border of the tongue (a 20×4 mm penetrating ulcer with 1 mm red borders, and a more anterior 5×6 mm ulcer) and a new 3 mm erosion on the right lateral border of the tongue with minimal erythema.

In April, 1998, topical AZA rinse was resumed (25 mg/ml, 5 ml t.i.d.) and the patient reported reduced oral sensitivity limited to the left lateral border of the tongue, which corresponded to a 5×15 mm superficial ulceration, with non-thickened, non-indurated margins. Patchy atrophy of the dorsal aspect of the tongue and mild lichenoid changes without erythema at sites of prior mucosal ulceration were present. Early in May he reported reduced oral sensitivity, and the clinical examination revealed atrophic mucosa of the dorsal aspect of the tongue and erythema of the lateral tongue borders, with resolution of the ulceration and mild erythema present on the cheeks.

Figure 3A:
FIGS. 3A-3D show the significantly improved oral GVHD symptoms at the last follow-up visit in June 1998 in the same patient as in FIGS. 1A-1D and 2A-2D.
Figure 3B:
Figure 3C:
Figure 3D:
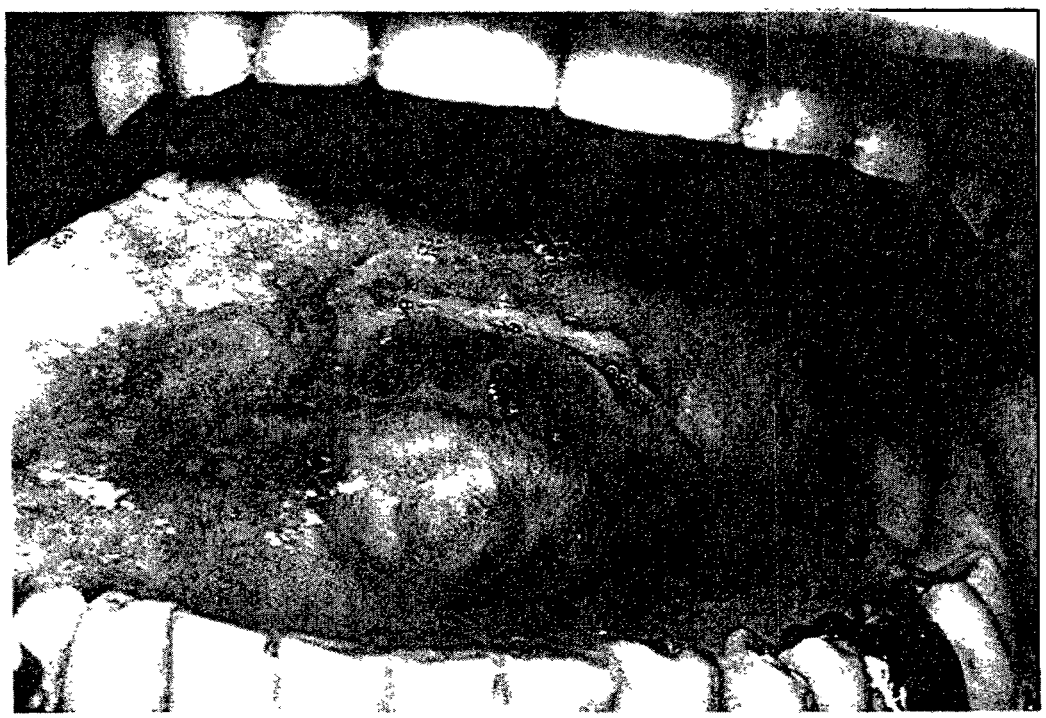

In May 1998 the patient was admitted to the hospital for pneumonia and was treated with IV antibiotics. At that time, the AZA suspension was replaced with AZA tablets (continuing dose of 25 mg t.i.d.), and prednisone was increased to 20 mg/day. Examination revealed minimal erythema and lichenoid striations in the cheeks and gingiva. A 15×4 mm ulceration was present on the left lateral border of the tongue, with clinically increased thickness of the border of the ulceration. Resumption of the AZA suspension and continuing systemic treatment was recommended. The oral ulcerations were virtually resolved at the last follow-up visit, following resumption of AZA suspension (FIGS. 3A-3D).

This case presented a number of the oral manifestations that may follow bone marrow transplantation, including oral infections (recurring candidosis and HSV-1 reactivations), hairy-leukoplakia-like changes on the tongue, altered taste that improved spontaneously after approximately 4 months following transplant; and findings of progressive systemic sclerosis [1, 2, 3, 22, 23]. Multiple early oral findings following transplant (at approximately Transplant Day+100) included taste alterations and oral sensitivity with oral ulcerations. The patient continued to have difficulty with oral GVHD, with lichenoid and lupus-like and systemic sclerosis-like manifestations. He had no difficulty with dry mouth. The case presented considerable oral involvement, including persisting ulceration of the tongue, which resulted in pain and affected the patient's quality of life. The oral symptoms and signs were improved only when systemic prednisone was increased; however, the oral ulceration on the tongue was not resolved. Various topical applications were also tried. These included topical steroids (dexamethasone rinse, fluocinonide gel, clobetasol ointment), a topical cyclosporin suspension [4], and topical cyclosporin in a mucoadhesive base (CsA in Zilactin) [5]. These approaches have been shown to improve local oral manifestations of GVHD [4,5]. However, all of these had only limited effects on the oral symptoms. An oral suspension of AZA was begun because of the persisting oral findings. No change in the systemic dose occurred, since the suspension was first introduced as a rinse and then swallowed. During these intervals, only minimal changes were made in use of other systemic immunosuppressives, other than at the patient's last admission to the hospital due to pneumonia, when the AZA suspension was replaced with AZA tablets, and prednisone was increased (from 10 to 20 mg/day). During this time, the tongue ulcer worsened, despite the increase in prednisone. Topical AZA was prescribed to maintain the systemic dosage level following discharge, when reduced doses of prednisone (10 mg/day) were provided. During periods when topical AZA was replaced with AZA by tablet, oral symptoms and signs of GVHD increased, and oral findings improved on several occasions with the resumption of topical application. When seen at last follow-up, the oral ulcerative lesion had improved despite the decreased prednisone dose.

The use of a topical formulation of azathioprine theoretically offers the benefit of increasing the therapeutic local effect without the need for an increased dosage of systemic immunosuppressive agents. It is possible that the absorption of this agent via oral mucosa may increase the systemic effect in cases where systemic dosing is not provided; although, in this instance, the suspension was swallowed in order to maintain the systemic dose previously administered in tablet form. The combination of agents in this case resulted in improved management of previously refractory oral GVHD, without change in systemic drugs and therefore with less risk of increased systemic side effects.

Additional Clinical Data:

Five other patients suffering from oral findings due to GVHD were treated with oral azathioprine solutions, using the method of the present invention. The patients were treated with 5 ml of a solution of AZA (5 mg/ml), three-four times daily. For each treatment, the mouth was rinsed for a period of time greater than 1 minute, and then the solution was expectorated. One patient (#5) was treated once with an oral rinse, and subsequently with a combination of an AZA rinse and AZA in a gel (5 mg/ml in a 3% methylcellulose base). The patients were not treated with any systemic immunosuppressant or steroid drug. The progress of each patient was reviewed at the times indicated. The results are shown in Table 1 below.

TABLE 1

| | | | | Patients with GVHD | | | | | | | |
| | | | AZA | Pre-Treatment Mucositis | | | Post-Treatment Mucositis | | | F/U | Estimated Global |
| Patient # | Age | Gender | Formulation | Ulcer | Erythema | Pain | Ulcer | Erythema | Pain | (weeks) | Improvement |
|---|---|---|---|---|---|---|---|---|---|---|---|
| 1 | 38 | F | rinse | 25 | 4 | 3 | 0 | 3 | 0 | 8 | 75% |
| 2 | 38 | M | rinse | 120 | 12 | 6 | 10 | 2 | 3 | 16 | 90% |
| 3 | 35 | M | nnse | 80 | 14 | 6 | 24 | 7 | 1 | 24 | 60% |
| 4 | 43 | M | rinse | 90 | 10 | 4 | 75 | 4 | 2 | 36 | 40% |

TABLE 1-continued

| | | | | Patients with GVHD | | | | | | | |
|---|---|---|---|---|---|---|---|---|---|---|---|
| | | | AZA | Pre-Treatment Mucositis | | | Post-Treatment Mucositis | | | F/U | Estimated Global |
| Patient # | Age | Gender | Formulation | Ulcer | Erythema | Pain | Ulcer | Erythema | Pain | (weeks) | Improvement |
| 5* | 45 | M | rinse | 183 | 2 | 4 | 90 | 2 | 2 | 8 | 40% |
| 5* | 45 | M | rinse + gel | 90 | 2 | 2 | 65 | 1 | 1 | 32 | 50% from rinse visit |

F/U = followup
Mucositis scores:
Ulcer — total ulceration all surfaces ($mm^2$)
Erythema — total of score for all surfaces
0 = none; 1 = mild; 2 = severe
Pain — VAS 0-10 scale; 0 = no pain, 10 = most severe pain imaginable
*Patient #5 treated initially with AZA rinse formulation, and thereafter with AZA rinse + gel.

All the patients demonstrated at least a 40% estimated global improvement after treatment with the method of the present invention, as compared to their condition prior to initiation of treatment. In particular, all the patients reported at least a 50% reduction in pain, and all but one at least 50% reduction in ulceration. The use of a combination of an AZA rinse with a gel containing AZA also was effective in reducing the ulceration associated with oral manifestations of GVHD (Patient #5). Surprisingly, the benefits of the present invention were achieved without the requirement for maintenance of a systemic level of either immunosuppressant or steroid drugs. Thus, the side effects associated with systemic administration of these drugs were avoided as well.

The method of the present invention was extended to the treatment of other conditions as well. One patient suffering from pemphigus vulgaris and one patient suffering from benign mucous membrane pemphigoid ("BMMP") were treated with the method of the present invention. The treatment procedures were as described above for the additional patients with GVHD, and also included no systemic doses of immunosuppressant or steroid drugs. The results are shown in Table 2.

In both cases shown in Table 2, a dramatic improvement was seen after treatment with the method of the present invention. In the pemphigus vulgaris patient, a 60% reduction in Estimated Global Improvement was attained after 8 weeks of treatment with an AZA rinse. In the pemphigoid case, the patient was virtually completely healed, with no ulceration or pain, and only very slight erythema, after treatment for 12 weeks. It is noteworthy that in this latter patient, the AZA was administered in the form of a gel. Therefore, in view of the beneficial results reported in Tables 1 and 2, AZA gel formulations, when tolerated, may represent an important alternative to the AZA rinse.

These data suggests that topical use of AZA may be an advantageous alternative for management of oral immune-mediated inflammatory conditions. In particular, the oral topical delivery of AZA may be beneficial for patients with oral chronic graft-versus-host disease, and also for other autoimmune oral mucosal diseases.

The present invention has been set forth in the form of its preferred embodiments. Other alternative embodiments may be devised, however, and are intended to be within the scope of this application. Furthermore, it is intended that modifications to the disclosed invention may be made without departing from the scope and spirit of the inventive concepts set forth herein. Throughout this application various publications and patents are cited. The contents of these publications and patents are hereby incorporated by reference into the present application.

TABLE 2

| | | | | Patients with Immune Oral Conditions Other Than GVHD | | | | | | | |
|---|---|---|---|---|---|---|---|---|---|---|---|
| | | | | AZA | Pre-Treatment Mucositis | | | Post-Treatment Mucositis | | F/U | Estimated Global |
| Patient # | Age | Gender | Condition | Formulation | Ulcer | Erythema | Pain | Ulcer | Erythema | Pain | (weeks) | Improvement |
| 6 | 31 | M | pemphigus vulgaris | rinse | 230 | 10 | 7.5 | 150 | 4 | 2 | 8 | 60% |
| 7 | 52 | M | BMMP | gel | 15 | 8 | 2 | 0 | 1 | 0 | 12 | 90% |

BMMP — benign mucous membrane pemphigoid

REFERENCES

1. Woo, S B, Lee, S J, Schubert, M M. Graft-vs.-host disease. Crit Rev Oral Biol Med 1997; 8(2):201-216.
2. Schubert, M M, Sullivan, K M. Recognition, incidence, and management of oral graft-versus-host disease. NCI Monogr 1990; (9):135-143.

3. Nakamura, S, Hiroki, A, Shinohara, M, et al. Oral involvement in chronic graft-versus-host disease after allogeneic bone marrow transplantation. Oral Surg Oral Med Oral Pathol Oral Radiol Endod 1996; 82(5):556-563.
4. Epstein J B, Reece, D E. Topical cyclosporin A for treatment of oral chronic graft-versus-host disease. Bone Marrow Transplant 1994; 13:81-86.
5. Epstein J B, Truelove, E L. Topical cyclosporin in a bioadhesive for treatment of oral lichenoid mucosal reactions. Oral Surg Oral Med Oral Pathol Oral Radiol Endod 1996; 82:532-536.
6. Sandborn W J. A review of immune modifier therapy for inflammatory bowel disease: azathioprine, 6-mercaptourine, cyclosporin, and methotrexate. Am J Gastroenterol 1996; 91(3):423-433.
7. Winklestein A. The effects of azathioprine and 6-MP on immunity. J Immunopharmacol 1979; 1:429-454.
8. Brogan M, Hiserodt J, Oliver M, et al. The effect of 6-mercaptopurine on natural killer-cell activities in Crohn's disease. J Clin Immunol 1985; 5:204-11.
9. Brogan M, Stevens R, Hiserodt J, et al. Effects of 6-MP on the impaired in vivo humoral responsiveness in Crohn's disease. Gastroenterol 1984; 86:A1035.
10. Lozada F. Prednisone and azathioprine in the treatment of patients with vesiculoerosive oral diseases. Oral Surg Oral Med Oral Pathol 1981; 52(3):257-260.
11. Robinson J R, Lozada-Nur F, Frieden I. Oral pemphigus vulgaris. A review of the literature and a report on the management of 12 cases. Oral Surg Oral Med Oral Pathol Oral Radiol Endod 1997; 84:349-355.
12. Lear, J T, English, J S C. Erosive and generalized lichen planus responsive to azathioprine. Clin Exper Derm 1996; 21:56-57.
13. Allen L V Jr, Erickson M A. Stability of acetazolamide, allopurinol, azathioprine, clonazepam, and flucytosine in extemporaneously compounded oral liquids. Am J Health-Syst Pharm 1996; 53:1944-1949.
14. Eggleston D J, Nally F F. Treatment of aphthous ulceration with topical azathioprine. A double blind trial. Br J Oral Surg 1972; 9(3):233-236.
15. Suchko V I, Mashchenko I S. Local use of an azathioprine suspension in a dimexide solution in the combined treatment of parodontosis. Stomologica (Mosk) 1981; 60(3): 28-30.
16. Elliot J H, Leibowitz H M. Chemotherapeutic immunosuppression of the corneal graft reaction. 3. Topical azathioprine. Arch Opthalmol 1966; 76(5):709-711.
17. Mackay I R, Bignell J L, Smith P H, Crawford B A. Prevention of corneal-graft failure with the immunosuppressive drug azathioprine. Lancet 1967; 514 (2):479-482.
18. Choi P M, Targan S R. Immunomodulator therapy in inflammatory bowel disease. Dig Dis Sci 1994; 39(9): 1885-1892.
19. Stotland B R, Lichtenstein G R. Newer treatments for inflammatory bowel disease. Prim Care 1996; 3(3):577-608.
20. Zins B J, Sandborn W J, McKinney J A, et al. A dose-ranging study of azathioprine pharmacokinetics after single-dose administration of a delayed-release oral formulation. J Clin Pharmacol 1997; 37:38-46.
21. Van Os E C, Zins W J, Sandborn W J, et al. Azathioprine pharmacokinetics after intravenous, oral, delayed release oral and rectal foam administration. Gut 1996; 39:63-68.
22. Epstein J B, Priddy R W, Sherlock C H. Hairy leukoplakia-like lesions in immunosuppressed patients following bone marrow transplantation. Transplantation 1988; 46:462-4.
23. Epstein J B, Sherlock C H, Wolber R A. Hairy leukoplakia after bone marrow transplantation. Oral Surg Oral Med Oral Pathol 1993; 75:690-5.
24. Scully, C, Paes de LImeida, O, Porter, S R, Gilkes, J J H. Pemphigus vulgaris: the manifestations and long-term management of 55 patients with oral lesions. Br J Dermatol 1999; 140:84-89.
25. Lever, W F. Pemphigus and pemphigoid. A review of the advances made since 1964. J Amer Acad Dermatol. 1979; 1(1):2-31.
26. Anstey, A, Lear, J T. Azathioprine: clinical pharmacology and current indications in autoimmune disorders. BioDrugs 1998; 9(1):33-47.
27. Glied, M, Rico, J M. Treatment of autoimmune blistering diseases. Dermatol Clin 1999; 17(2):431-330.
28. Sharpe et al. Method for treating diseases mediated by proteases. U.S. Pat. No. 5,637,616. Issued Jun. 10, 1997.

What is claimed is:

1. A method for treating graft-versus-host disease of the mouth, comprising: swishing for at least one minute in the mouth of a patient in need of such treatment an effective amount of a liquid formulation consisting of a pharmaceutically acceptable carrier, a member selected from the group consisting of azathioprine, 6-mercaptopurine, 6-thioguanine nucleotide, a pharmaceutically acceptable salt of azathioprine, a pharmaceutically acceptable salt of 6-mercaptopurine, and a pharmaceutically acceptable salt of 6-thioguanine nucleotide.

2. The method of claim 1, wherein said formulation includes a member selected from the group consisting of azathioprine, 6-mercaptopurine, and 6-thioguanine nucleotide.

3. The method of claim 1, wherein said formulation includes azathioprine or a pharmaceutically acceptable salt thereof.

4. The method of claim 3, wherein said azathioprine or a pharmaceutically acceptable salt thereof is in a solution or suspension at a concentration between 0.5 and 50 mg/ml.

5. The method of claim 3, wherein said azathioprine or a pharmaceutically acceptable salt thereof is administered at a dosage between 50 and 250 mg/day.

6. The method of claim 1, wherein said swishing step includes rinsing the mouth of said patient with said formulation for at least one minute; and swallowing said formulation after said step of rinsing.

7. The method of claim 3, wherein said swishing step includes rinsing the mouth with said formulation for at least one minute, and thereafter expectorating said formulation without swallowing.

8. The method of claim 1, further comprising systemically administering an effective amount of a member selected from the group consisting of a steroidal anti-inflammatory compound, a non-steroidal anti-inflammatory compound, and an immunosuppressant.

* * * * *